United States Patent
Patra et al.

(10) Patent No.: US 6,921,843 B2
(45) Date of Patent: Jul. 26, 2005

(54) PROCESS FOR THE PREPARATION OF DIEMETHYL CUMENES

(75) Inventors: Chitta Ranjan Patra, Maharashtra (IN); Rajiv Kumar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/024,537

(22) Filed: Dec. 21, 2001

(65) Prior Publication Data

US 2003/0176750 A1 Sep. 18, 2003

(51) Int. Cl.⁷ .................................................. C07C 2/66
(52) U.S. Cl. ..................................................... 585/467
(58) Field of Search .......................................... 585/467

(56) References Cited

U.S. PATENT DOCUMENTS 3,553,274 A    1/1971  Lewis et al. ................. 260/650
5,118,896 A  * 6/1992  Steigelmann et al. ....... 585/467

FOREIGN PATENT DOCUMENTS

| EP | 0439632 A1 | 12/1989 |
| EP | 0371738 A2 | 6/1990 |
| EP | 0538518 A1 | 4/1993 |
| EP | 0940178 A1 | 3/1998 |
| EP | 1069099 A1 | 1/2001 |
| EP | 1069100 A1 | 1/2001 |

* cited by examiner

*Primary Examiner*—Thuan D Dang
(74) *Attorney, Agent, or Firm*—Nixon & Vanderhye, P.C.

(57) ABSTRACT

The present invention relates to a process for the preparation of dimethylcumenes comprising alkylating a substrate comprising of one or more xylene isomers with an alkylating agent in the presence of a solid acid zeolite catalyst selected from ultrastable zeolite Y (Si/Al=5 to 50) and Beta (Si/Al=10–120), and separating the products formed in vapour phase.

17 Claims, No Drawings

PROCESS FOR THE PREPARATION OF DIEMETHYL CUMENES

FIELD OF THE INVENTION

The present invention relates to a process for the preparation of dimethylcumenes. More particularly, the present invention relates to a process for the preparation of dimethylcumenes by the catalytic isopropylation of xylenes using isopropylene as the alkylating agent over a solid catalyst.

BACKGROUND OF THE INVENTION

Dimethylcumenes are useful raw materials for the production of xylenols, pesticides, pharmaceuticals, perfumery, heat transfer media, polymers and special solvents. Xylenols are an important class of phenolic substrates useful as raw materials for making phenolic resins having specific thermoelastic properties.

The most common method for the preparation of dimethylcumenes is by the alkylation of xylene carried out in the presence of metal halides, $AlCl_3$, $ZnCl_2$ and inorganic acids HCl, $H_2SO_4$ [(i) Journal of Chemical Education, Vol. 70 (6), pages A 152–154, 1993; and (ii) U.S. Pat. No. 5,300,717, which disclose a process for the preparation of dixylylpropane wherein one step comprises the formation of 1,2-dimethyl-4-isopropylbenzene from o-xylene and propene in the presence of conventional Friedel Crafts catalysts such as $BF_3$—$H_3PO_4$, $AlCl_3$—$CH_3NO_2$). This process suffers from the disadvantage that it is environmentally hazardous, giving rise to problems in terms of handling, safety, corrosion and waste disposal.

Rare earth modified zeolites such as (Nd—Na—Y) are reported as catalyzing the alkylation, including the isopropylation of o-xylene (Dokl Akad. Nauk., Vol. 335 (3), 1994, p. 322–325<CA: 121:182357). In this case, although the isopropylation of o-xylene resulted in the formation of a mixture of dimethylcumenes, alkylation could not be obtained when p-xylene was used as a substrate. The disadvantage of this catalyst system is its inactivity for other xylene isomers such p-xylene. The conversions and selectivity are also low for the desired dimethylcumene isomers. Additionally, this catalyst is less active for isopropylation as compared to tertiary butylation of o-xylene. Solid catalysts such as $TiO_2$—$SiO_2$—$Al_2O_3$ (Tisial) and $MoO_3$—$SiO_2$—$Al_2O_3$ (Mosial) are also reported for the catalytic alkylation of benzene, toluene and xylene isomers with $C_2$, $C_3$, and $C_4$ aliphatic alcohols (Indian Journal of Chemistry, Vol. 33B, pp. 1053–1061, 1994). However, the yield of desired mono dimethylcumenes is low (ca.50%).

In view of the above-mentioned drawbacks and limitations of the above process, it was found desirable to develop an improved process for the production of dimethylcumene isomers with isopropanol using a solid acid catalyst, either in batch reactor or in fixed bed down flow reactor.

OBJECTS OF THE INVENTION

The main object of the present invention is to provide an improved process for the preparation of dimethylcumenes overcoming the above-mentioned drawbacks by contacting xylene isomers with isopropanol using a solid acid catalyst with high yield and selectivity.

It is another object of the present invention to sue solid heterogeneous catalyst which are reusable by simple thermal treatment in the presence of air.

Yet another object of the invention is to provide a process for the preparation of dimethylcumenes in either batch reactor or in a continuous fixed bed reactor.

SUMMARY OF THE INVENTION

Accordingly, the present invention relates to a process for the preparation of dimethylcumenes comprising alkylating a substrate comprising of one or more xylene isomers with an alkylating agent in the presence of a solid acid zeolite catalyst, and separating the products formed in vapour phase.

In one embodiment of the invention, said substrate and alkylating agent are contacted with said solid acid zeolite catalyst at a temperature in the range of 80–250° C. and for a period of at least 1 hour.

In another embodiment of the invention, the product is separated from the vapour phase by condensation at a temperature in the range of 0–3° C.

In yet another embodiment of the invention, the substrate is selected from o-xylene, m-xylene, p-xylene and any mixture thereof.

In another embodiment of the invention, the solid acid zeolite catalyst comprises a solid heterogeneous solid acid catalyst selected from ultrastable zeolite Y (Si/Al=5 to 50) and Beta (Si/Al=10–120), preferably, the Si/Al ratio in said catalyst is between 5 to 20.

In another embodiment of the invention, the alkylating agent is selected from propylene and propyl alcohols such as isopropanol and n-propanol.

In another embodiment of the invention, the temperature of the reaction is in the range of 100–200° C., preferably 120–180° C.

In yet another embodiment of the invention, the molar ratio of xylene substrate to the alkylating agent in the feed is in the range of from 1:2 to 20:1, preferably 1:1 to 10:1, more preferably, in the range of 1:2 to 5:1.

In another embodiment of the invention, the weight hourly space velocity (WHSV) of the feed is in the range of 0.5 to 30 $h^{-1}$, preferably 1 to 20 $h^{-1}$, more preferably 2 to 10 $h^{-1}$.

In a further embodiment of the invention, the alkylation reaction is carried out in a fixed bed reactor or a batch reactor.

In yet another embodiment of the invention, p-xylene is alkylated using isopropanol in the presence of zeolite beta catalyst.

In another embodiment of the invention, m-xylene and o-xylene are alkylated using isopropanol as the alkylating agent in the presence of ultrastable zeolite Y (USY) as catalyst.

In yet another embodiment of the invention, a mixture of p-xylene and isopropyl alcohol in a molar ratio of 4:1 is reacted in a fixed bed reactor in the presence of ultrastable zeolite Y (hereinafter USY) catalyst.

DETAILED DESCRIPTION OF THE INVENTION

The present invention provides a process for the preparation of dimethylcumenes by reacting a xylene isomer or a mixture of xylene isomers with an alkylating agent in presence of a solid acid zeolite catalyst. The reaction can be carried out either in a fixed bed reactor or a batch reactor. Preferably, the temperature of the alkylation reaction is in the range of 80–250° C., and the molar ratio of the xylene isomer substrate to the alkylating agent in the feed is in the range of 1:2 to 20:1. Reaction is carried out at a WHSV of 0.5 to 30 $h^{-1}$. Propylene or propyl alcohols such as isopropanol or n-propanol can be used as alkylating agents.

The novelty and inventive step in this invention resides in the use of solid acid zeolite catalysts such as zeolite USY or zeolite beta as the catalysts for alkylation reaction. Solid acid zeolite catalysts show very high catalytic activity and selectivity in alkylation of all xylene isomers, unlike in the prior art wherein only o-xylene and not m- or p-xylenes could be alkylated using Nd—Na—Y zeolite catalyst. While both zeolite USY and zeolite Beta are suitable for propylation of xylene isomers, it is observed that zeolite Beta is more suitable for isopropylation of p-xylene and zeolite USY is preferred for isopropylation of m- and p-xylene. Without wishing to be bound by any theory, it is believed that this could be due to the slightly small pore openings of zeolite Beta as compared to zeolite USY. p-xylene being the smallest among all the xylenes, has faster ingress into zeolite Beta when compared to ortho- or meta-isomers. This diffusional limitation is not present in the case of zeolite USY. H-Mord. and MFI are not as good catalysts as zeolite Beta or zeolite USY for the alkylation reaction of this invention, due to their smaller pore size. p-xylene yields only one dimethylcumene isomer, 2,5 dimethylcumene since all regio positions are the same. o-xylene yields 2,3 dimethylecumene and 3,4 dimethylcumene isomers as the primary products. While in principle m-xylene can yield three dimethylcumene isomers, 2,4 dimethylcumene, 2,6 dimethylcumene and 3,5 dimethylcumene, only two isomers, 2,4 dimethylcumene, 2,6 dimethylcumene are formed as primary products since the alkylation is an ortho-para directing electrophilic substitution reaction and the regio position 3,5 in m-xylene is deactivated due to the meta position from both the methyl groups in m-xylene.

The following examples are provided to illustrate the invention and should not be construed as limiting the scope of the invention.

EXAMPLE 1

This example illustrates effect of time on stream (TOS) on conversion and product selectivity in isopropylation of p-xylene. USY catalyst (0.5 g) was loaded into the reactor such that the catalyst bed was sandwiched between inert porcelain beads. A mixture of p-xylene and isopropyl alcohol in a 4:1 molar ratio was introduced into fixed bed reactor by syringe pump (Sage Instruments, Model 352, USA) in a continuous manner in presence of inert carrier gas (nitrogen, flow=35 ml/min) at a WHSV of 6.48 $h^{-1}$ and a temperature of 140° C. for a period of 8 hours. Product samples were collected periodically (Table I below), chilled at 0° C. and analyzed by gas chromatograph (Shimadzu GC-14B) using flame ionization detector and 3 m×⅛" packed column with 5% bentone and 5% DIDP on chromosorb WHP, with mesh size of 801100. Results of the reaction are given in Table I below.

TABLE I

Effect of TOS on conversion and product selectivity in the isopropylation of p-xylene over zeolite USY

| | Time on stream | | | |
|---|---|---|---|---|
| Conversion or selectivity (mole %) | 1 h | 3 h | 5 h | 8 h |
| Conversion of p-xylene | 16.2 | 16.5 | 14.6 | 10.0 |
| Selectivity of dimethylcumenes in total products[a] | 94.2 | 88.8 | 87.8 | 84.0 |
| Selectivity of 2,5 dimethylcumene among DMC's | 100 | 100 | 100 | 100 |

TABLE I-continued

Effect of TOS on conversion and product selectivity in the isopropylation of p-xylene over zeolite USY

| | Time on stream | | | |
|---|---|---|---|---|
| Conversion or selectivity (mole %) | 1 h | 3 h | 5 h | 8 h |
| Selectivity of other products in total products | 5.8 | 11.2 | 12.2 | 16.0 |
| % yield of DMC in total products w.r.t. limiting reagent, i.e. isopropylating agent | 61.2 | 58.8 | 51.2 | 33.6 |

[a]the remaining products were mainly other isomerised and disproportionated products of xylene along with diisopropyl xylene (DIPX).

EXAMPLE 2

This example illustrates effect of temperature on conversion and product selectivity in isopropylation of p-xylene. USY catalyst (0.5 g) was loaded into reactor such that the catalyst bed was sandwiched between inert porcelain beads. A mixture of p-xylene and isopropyl alcohol in 4:1 molar ratio was introduced into fixed bed reactor by syringe pump (Sage Instruments, Model 352, USA) in continuous manner in presence of inert carrier gas (nitrogen, flow=35 ml/min) at WHSV of 6.48 $h^{-1}$ and at different temperatures (Table II) for a period of 1 hour. Products were chilled at 0° C. and analyzed by gas chromatograph using flame ionization detector. Results of reaction are given in Table II.

TABLE II

Effect of temperature on conversion and product selectivity in the isopropylation of p-xylene over zeolite USY

| | Temperature, ° C. | | | |
|---|---|---|---|---|
| Conversion or selectivity (mole %) | 120 | 140 | 160 | 180 |
| Conversion of p-xylene | 6.9 | 16.2 | 22.6 | 28.0 |
| Selectivity of dimethylcumenes in total products[a] | 96.5 | 94.2 | 78.6 | 56.1 |
| Selectivity of 2,5 dimethylcumene among DMC's | 100 | 100 | 97.0 | 89.0 |
| Selectivity of other products in total products | 3.5 | 5.8 | 21.4 | 43.9 |
| % yield of DMC in total products w.r.t. limiting reagent, i.e. isopropylating agent | 26.8 | 61.2 | 71.2 | 62.8 |

[a]the remaining products were mainly other isomerised and disproportionated products of xylene along with diisopropyl xylene (DIPX).

EXAMPLE 3

USY catalyst (0.5 g) was loaded into the reactor such that the catalyst bed was sandwiched between inert porcelain beads. A mixture of p-xylene and isopropyl alcohol in a 4:1 molar ratio was introduced into fixed bed reactor by syringe pump (Sage Instruments, Model 352, USA) in a continuous manner in the presence of inert carrier gas (nitrogen, flow=35 ml/min) at different WHSV (See Table III) and a temperature of 140° C. for 1 hour. Product was chilled at 0° C. and analyzed by gas chromatograph using flame ionization detector. Results of reaction are given in Table III.

TABLE III

Effect of space velocity on conversion and product selectivity
in the isopropylation of p-xylene over zeolite USY

|  | WHSV, h$^{-1}$ | | |
|---|---|---|---|
| Conversion or selectivity (mole %) | 3.2 | 6.5 | 12.9 |
| Conversion of p-xylene | 24.3 | 16.2 | 11.8 |
| Selectivity of dimethylcumenes in total products[a] | 90.5 | 94.2 | 96.2 |
| Selectivity of 2,5 dimethylcumene among DMC's | 98 | 100 | 100 |
| Selectivity of other products in total products | 9.5 | 5.8 | 3.8 |
| % yield of DMC in total products w.r.t. limiting reagent, i.e. isopropylating agent | 88.0 | 61.2 | 45.6 |

[a]the remaining products were mainly other isomerised and disproportionated products of xylene along with diisopropyl xylene (DIPX).

EXAMPLE 4

This example illustrates effect of molar ratio of p-xylene to isopropanol on conversion and product selectivity in isopropylation of p-xylene. USY catalyst (0.5 g) was loaded into the reactor such that catalyst bed was sandwiched between inert porcelain beads. A mixture of p-xylene and isopropyl alcohol with different molar ratio (Table IV) was introduced into fixed bed reactor by syringe pump (Sage Instruments, Model 352, USA) in a continuous manner in the presence of inert carrier gas (nitrogen, flow=35 ml/min) at a WHSV of 6.48 h$^{-1}$ and a temperature of 140° C. for a period of 8 hours. Products were chilled at 0° C. and analyzed by gas chromatograph using flame ionization detector. Results of reaction are given in Table IV.

TABLE IV

Effect of molar ratio of p-xylene and isopropanol
on conversion and product selectivity in the isopropylation
of p-xylene over zeolite USY

|  | p-xylene/isopropanol (molar) | | | |
|---|---|---|---|---|
| Conversion or selectivity (mole %) | 2:1 | 4:1 | 8:1 | 10:1 |
| Theoretical maximum conversion | 50 | 25 | 12.5 | 10 |
| Conversion of p-xylene | 35.4 | 16.2 | 9.7 | 7.1 |
| Selectivity of dimethylcumenes in total products[a] | 76.8 | 94.2 | 95.6 | 100 |
| Selectivity of 2,5 dimethylcumene among DMC's | 97.3 | 100 | 100 | 100 |
| Selectivity of other products in total products | 23.2 | 5.8 | 4.4 | 0 |
| % yield of DMC in total products w.r.t. limiting reagent, i.e. isopropylating agent | 54.4 | 61.2 | 74.4 | 71.0 |

[a]the remaining products were mainly other isomerised and disproportionated products of xylene along with diisopropyl xylene (DIPX).

EXAMPLE 5

This example illustrates effect of time on stream (TOS) on conversion and product selectivity in isopropylation of m-xylene. USY catalyst (0.5 g) was loaded into a reactor such that the catalyst bed was sandwiched between inert porcelain beads. A mixture of m-xylene and isopropyl alcohol in a 4:1 molar ratio was introduced into fixed bed reactor by a syringe pump (Sage Instruments, Model 352, USA) in a continuous manner in presence of inert carrier gas (nitrogen, flow=35 ml/min) at a WHSV of 6.48 h$^{-1}$ and a temperature of 140° C. for a period of 1–8 hours. Products were chilled at 0° C., collected every hour up to 8 hours and analyzed by gas chromatograph (Shimadzu GC-14B) using flame ionization detector and 3 m×⅛" packed column with 5% bentone and 5% DIDP on chromosorb WHP, with mesh size of 801100. Results of the reaction are given in Table V.

TABLE V

Effect of TOS on conversion and product selectivity
in the isopropylation of m-xylene over zeolite USY

|  | Time on stream | | | |
|---|---|---|---|---|
| Conversion or selectivity (mole %) | 1 h | 3 h | 5 h | 8 h |
| Conversion of m-xylene | 16.6 | 19.1 | 15.7 | 14.2 |
| Selectivity of dimethylcumenes in total products[a] | 91.0 | 93.0 | 91.7 | 87.0 |
| Selectivity of 2,4 dimethylcumene among DMC's | 78.9 | 56.1 | 52.8 | 29.6 |
| Selectivity of 2,6 dimethylcumene among DMC's | 21.1 | 43.9 | 47.2 | 70.4 |
| Selectivity of other products in total products | 9.0 | 7.0 | 8.3 | 13.0 |
| 2.4 DMC/2.6 DMC | 3.7 | 1.3 | 1.1 | 0.4 |
| % yield of DMC in total products w.r.t. limiting reagent, i.e ispropylating agent | 60.0 | 70.8 | 57.6 | 49.6 |

[a]the remaining products were mainly other isomerised and disproportionated products of xylene along with diisopropyl xylene (DIPX).

EXAMPLE 6

This example illustrates effect of temperature on conversion and product selectivity in isopropylation of m-xylene. USY catalyst (0.5 g) was loaded into reactor such that the catalyst bed was sandwiched between inert porcelain beads. A mixture of m-xylene and isopropyl alcohol in 4:1 molar ratio was introduced into fixed bed reactor by a syringe pump (Sage Instruments, Model 352, USA) in continuous manner in presence of an inert carrier gas (nitrogen, flow=35 ml/min) at WHSV of 6.48 h$^{-1}$ and at different temperatures (Table VI) for a period of 1 hour. Products were chilled at 0° C. and analyzed by gas chromatograph using flame ionization detector. Results of reaction are given in Table VI.

TABLE VI

Effect of temperature on conversion and product selectivity
in the isopropylation of m-xylene over zeolite USY

|  | Temperature, ° C. | | | |
|---|---|---|---|---|
| Conversion or selectivity (mole %) | 120 | 140 | 160 | 180 |
| Conversion of m-xylene | 12.3 | 16.5 | 27.3 | 29.3 |
| Selectivity of dimethylcumenes in total products[a] | 93.3 | 91.0 | 88.0 | 64.1 |
| Selectivity of 2,4 dimethylcumene among DMC's | 58.8 | 78.9 | 75.3 | 67.2 |
| Selectivity of 2,6 dimethylcumene among DMC's | 41.2 | 21.1 | 24.7 | 32.8 |
| Selectivity of other products in total products | 6.7 | 9.0 | 12.0 | 35.9 |
| 2,4 DMC/2,6 DMC | 1.4 | 3.7 | 3.1 | 2.0 |
| % yield of DMC in total products w.r.t. limiting reagent, i.e. isopropylating agent | 46.0 | 60.0 | 96.1 | 75.2 |

[a]the remaining products were mainly other isomerised and disproportionated products of xylene along with diisopropyl xylene (DIPX).

EXAMPLE 7

USY catalyst (0.5 g) was loaded into the reactor such that the catalyst bed was sandwiched between inert porcelain beads. A mixture of m-xylene and isopropyl alcohol in a 4:1 molar ratio was introduced into the fixed bed reactor by a syringe pump (Sage Instruments, Model 352, USA) in a continuous manner in the presence of an inert carrier gas (nitrogen, flow=35 ml/min) at different WHSV (Table VII) and a temperature of 140° C. for 1 hour.

Product was chilled at 0° C. and analyzed by gas chromatograph using flame ionization detector. Results of the reaction are given in Table VII below.

TABLE VII

Effect of space velocity on conversion and product selectivity in the isopropylation of m-xylene over zeolite USY

| | WHSV, h$^{-1}$ | | |
|---|---|---|---|
| Conversion or selectivity (mole %) | 3.2 | 6.5 | 12.9 |
| Conversion of m-xylene | 20.7 | 16.5 | 10.7 |
| Selectivity of dimethylcumenes in total products[a] | 90.0 | 91.0 | 93.8 |
| Selectivity of 2,4 dimethylcumene among DMC's | 75.8 | 78.9 | 53.3 |
| Selectivity of 2,6 dimethylcumene among DMC's | 24.2 | 21.1 | 46.5 |
| Selectivity of other products in total products | 10.0 | 9.0 | 6.2 |
| 2,4 DMC/2,6 DMC | 3.1 | 3.7 | 1.2 |
| % yield of DMC in total products w.r.t. limiting reagent, i.e. isopropylating agent | 74.4 | 60.0 | 40.0 |

[a]the remaining products were mainly other isomerised and disproportionated products of xylene along with diisopropyl xylene (DIPX).

EXAMPLE 8

This example illustrates the effect of molar ratio of m-xylene to isopropanol on conversion and product selectivity in isopropylation of m-xylene. USY catalyst (0.5 g) was loaded into the reactor in such a way that the catalyst bed was sandwiched between inert porcelain beads. A mixture of m-xylene and isopropyl alcohol with different molar ratio (Table VIII) was introduced into fixed bed reactor by a syringe pump (Sage Instruments, Model 352, USA) in a continuous manner in the presence of an inert carrier gas (nitrogen, flow=35 ml/min) at a WHSV of 6.48 h$^{-1}$ and a temperature of 140° C. for a period of 8 hours. The product were chilled at 0° C. and analyzed by gas chromatograph using flame ionization detector. Results of the reaction are given in Table VIII.

TABLE VIII

Effect of molar ratio of m-xylene and isopropanol on conversion and product selectivity in the isopropylation of m-xylene over zeolite USY

| | m-xylene/isopropanol (molar) | | | |
|---|---|---|---|---|
| Conversion or selectivity (mole %) | 2:1 | 4:1 | 8:1 | 10:1 |
| Theoretical maximum conversion | 50 | 25 | 12.5 | 10 |
| Conversion of m-xylene | 19.1 | 16.5 | 11.3 | 6.7 |
| Selectivity of dimethylcumenes in total products[a] | 74.6 | 91.0 | 98.0 | 99.0 |
| Selectivity of 2,4 dimethylcumene among DMC's | 54.2 | 78.9 | 71.1 | 72.0 |
| Selectivity of 2,6 dimethylcumene among DMC's | 45.8 | 21.1 | 28.9 | 28.0 |
| Selectivity of other products in total products | 25.4 | 9.0 | 2.0 | 1.0 |
| 2,4 DMC/2,6 DMC | 1.2 | 3.7 | 2.5 | 2.6 |
| % yield of DMC in total products w.r.t. limiting reagent, i.e. isopropylating agent | 28.6 | 60.0 | 88.8 | 66.0 |

[a]the remaining products were mainly other isomerised and disproportionated products of xylene along with diisopropyl xylene (DIPX).

EXAMPLE 9

This example illustrates effect of time on stream (TOS) on conversion and product selectivity in isopropylation of o-xylene. USY catalyst (0.5 g) was loaded into the reactor such that the catalyst bed was sandwiched between inert porcelain beads. A mixture of o-xylene and isopropyl alcohol in a 4:1 molar ratio was introduced into fixed bed reactor by a syringe pump (Sage Instruments, Model 352, USA) in a continuous manner in the presence of inert carrier gas (nitrogen, flow=35 ml/min) at a WHSV of 6.48 h$^{-1}$ and a temperature of 140° C. for a period of 1–8 hours. Products were chilled at 0° C., collected every hour up to 8 hours and analyzed by gas chromatograph (Shimadzu GC-14B) using flame ionization detector and 3 m×⅛" packed column with 5% bentone and 5% DIDP on chromosorb WHP, with mesh size of 801100. Results of reaction are given in Table IX.

TABLE IX

Effect of TOS on conversion and product selectivity in the isopropylation of o-xylene over zeolite USY

| | Time on stream | | | |
|---|---|---|---|---|
| Conversion or selectivity (mole %) | 1 h | 3 h | 5 h | 8 h |
| Conversion of o-xylene | 15.6 | 18.6 | 16.9 | 15.1 |
| Selectivity of dimethylcumenes in total products[a] | 85.1 | 85.0 | 83.8 | 80.0 |
| Selectivity of 3,4 dimethylcumene among DMC's | 92.6 | 90.9 | 89.7 | 85.4 |
| Selectivity of 2,3 dimethylcumene among DMC's | 6.4 | 8.4 | 9.7 | 14.1 |
| Selectivity of other products in total products | 14.9 | 15.0 | 16.2 | 20.0 |
| 3,4 DMC/2,3 DMC | 14.5 | 10.8 | 9.2 | 6.1 |
| % yield of DMC in total products w.r.t. limiting reagent, i.e. isopropylating agent | 53.2 | 63.2 | 56.8 | 48.4 |

[a]the remaining products were mainly other isomerised and disproportionated products of xylene along with diisopropyl xylene (DIPX).

EXAMPLE 10

This example illustrates effect of temperature on conversion and product selectivity in isopropylation of o-xylene. USY catalyst (0.5 g) was loaded into reactor such that the catalyst bed was sandwiched between inert porcelain beads. A mixture of o-xylene and isopropyl alcohol in 4:1 molar ratio was introduced into fixed bed reactor by a syringe pump (Sage Instruments, Model 352, USA) in continuous manner in presence of inert carrier gas (nitrogen, flow=35 ml/min) at WHSV of 6.48 h$^{-1}$ and at different temperatures (Table X) for a period of 1 hour. Products were chilled at 0°

C. and analyzed by gas chromatograph using flame ionization detector. Results of reaction are given in Table X.

TABLE X

Effect of temperature on conversion and product selectivity in the isopropylation of o-xylene over zeolite USY

| | Temperature, °C. | | | |
|---|---|---|---|---|
| Conversion or selectivity (mole %) | 120 | 140 | 160 | 180 |
| Conversion of o-xylene | 4.6 | 15.6 | 20.7 | 25.0 |
| Selectivity of dimethylcumenes in total products[a] | 86.0 | 85.1 | 83.0 | 75.7 |
| Selectivity of 3,4 dimethylcumene among DMC's | 72.3 | 92.6 | 95.0 | 95.6 |
| Selectivity of 2,3 dimethylcumene among DMC's | 26.5 | 6.4 | 2.9 | 2.6 |
| Selectivity of other products in total products | 14.0 | 14.9 | 17.0 | 24.3 |
| 3,4 DMC/2,3 DMC | 2.7 | 14.5 | 32.8 | 36.8 |
| % yield of DMC in total products w.r.t. limiting reagent, i.e. isopropylating agent | 16.0 | 53.2 | 68.8 | 75.6 |

[a]the remaining products were mainly other isomerised and disproportionated products of xylene along with diisopropyl xylene (DIPX).

EXAMPLE 11

USY catalyst (0.5 g) was loaded into the reactor such that the catalyst bed was sandwiched between inert porcelain beads. A mixture of o-xylene and isopropyl alcohol in a 4:1 molar ratio was introduced into fixed bed reactor by a syringe pump (Sage Instruments, Model 352, USA) in a continuous manner in the presence of inert carrier gas (nitrogen, flow=35 ml/min) at different WHSV (Table XI) and a temperature of 140° C. for 1 hour. Product was chilled at 0° C. and analyzed by gas chromatograph using flame ionization detector. Results of reaction are given in Table XI.

TABLE XI

Effect of space velocity on conversion and product selectivity in the isopropylation of o-xylene over zeolite USY

| | WHSV, h$^{-1}$ | | |
|---|---|---|---|
| Conversion or selectivity (mole %) | 3.2 | 6.5 | 12.9 |
| Conversion of o-xylene | 24.3 | 15.6 | 6.4 |
| Selectivity of dimethylcumenes in total products[a] | 82.0 | 85.1 | 86.5 |
| Selectivity of 3,4 dimethylcumene among DMC's | 94.6 | 92.6 | 81.3 |
| Selectivity of 2,3 dimethylcumene among DMC's | 4.2 | 6.4 | 18.0 |
| Selectivity of other products in total products | 18.0 | 14.9 | 13.5 |
| 3,4 DMC/2,3 DMC | 22.5 | 14.5 | 4.5 |
| % yield of DMC in total products w.r.t. limiting reagent, i.e. isopropylating agent | 79.6 | 53.2 | 22.0 |

[a]the remaining products were mainly other isomerised and disproportionated products of xylene along with diisopropyl xylene (DIPX).

EXAMPLE 12

This example illustrates the effect of molar ratio of o-xylene to isopropanol on conversion and product selectivity in isopropylation of o-xylene. USY catalyst (0.5 g) was loaded into the reactor in such a way that the catalyst bed was sandwiched between inert porcelain beads. A mixture of o-xylene and isopropyl alcohol with different molar ratio (See Table XII) was introduced into the fixed bed reactor by a syringe pump (Sage Instruments, Model 352, USA) in a continuous manner in the presence of an inert carrier gas (nitrogen, flow=35 ml/min) at a WHSV of 6.48 h$^{-1}$ and a temperature of 140° C. for a period of 8 hours.

The product were chilled at 0° C. and analyzed by gas chromatograph using flame ionization detector. Results of the reaction are given in Table XII below.

TABLE XII

Effect of molar ratio of o-xylene and isopropanol on conversion and product selectivity in the isopropylation of o-xylene over zeolite USY

| | o-xylene/isopropanol (molar) | | | |
|---|---|---|---|---|
| Conversion or selectivity (mole %) | 2:1 | 4:1 | 8:1 | 10:1 |
| Theoretical maximum conversion | 50 | 25 | 12.5 | 10 |
| Conversion of o-xylene | 21.4 | 15.6 | 10.7 | 9.4 |
| Selectivity of dimethylcumenes in total products[a] | 82.0 | 85.1 | 86.0 | 89.3 |
| Selectivity of 3,4 dimethylcumene among DMC's | 86.5 | 92.6 | 93.4 | 94.6 |
| Selectivity of 2,3 dimethylcumene among DMC's | 13.5 | 6.4 | 6.6 | 5.4 |
| Selectivity of other products in total products | 18.0 | 14.9 | 14.0 | 10.7 |
| 3,4 DMC/2,3 DMC | 6.4 | 14.5 | 14.2 | 17.5 |
| % yield of DMC in total products w.r.t. limiting reagent, i.e. isopropylating agent | 35.0 | 53.2 | 73.6 | 84.0 |

[a]the remaining products were mainly other isomerised and disproportionated products of xylene along with diisopropyl xylene (DIPX).

EXAMPLE 13

This example illustrates effect of zeolite structure on conversion of p-xylene and the yield of dimethylcumene in the total products. Different catalysts (0.5 g) (Table XIII) were loaded into the reactor such that respective catalyst beds were sandwiched between inert porcelain beads. A mixture of p-xylene and isopropyl alcohol with molar ratio 4:1 was introduced into the fixed bed reactor by a syringe pump (Sage Instruments, Model 352, USA) in continuous manner in presence of inert carrier gas (nitrogen, flow=35 ml/min) at WHSV of 3.24 h$^{-1}$ and temperature of 140° C. for 1 hour.

The products were chilled at 0° C. and analyzed by gas chromatograph using flame ionization detector. Results of the reaction are given in Table XIII below.

TABLE XIII

Effect of different catalysts on conversion and product selectivity in the isopropylation of p-xylene

| | Catalysts | | | |
|---|---|---|---|---|
| Conversion or selectivity (mole %) | USY | H-Beta | H-Mord | H-ZSM-5 |
| Conversion of p-xylene | 24.3 | 21.9 | 11.2 | 0.2 |
| Selectivity of dimethylcumenes in total products[a] | 90.5 | 97.7 | 97.0 | — |
| Selectivity of 2,5 dimethylcumene among DMC's | 98.0 | 94.4 | 95.6 | — |
| Selectivity of other products in total products | 9.5 | 2.3 | 3.0 | — |
| % yield of DMC in total products w.r.t. limiting reagent, i.e. isopropylating agent | 88.0 | 85.6 | 10.9 | — |

[a]the remaining products were mainly other isomerised and disproportionated products of xylene along with diisopropyl xylene (DIPX).

EXAMPLE 14

This example illustrates effect of zeolite structure on conversion of m-xylene and the yield of dimethylcumenes.

Different catalysts (0.5 g) (Table XIV) were loaded into reactor such that the respective catalyst beds were sandwiched between inert porcelain beads. A mixture of m-xylene and isopropyl alcohol with molar ratio 4:1 was introduced into the fixed bed reactors by a syringe pump (Sage Instruments, Model 352, USA) in continuous manner in presence of an inert carrier gas (nitrogen, flow=35 ml/min) at WHSV of 3.24 h$^{-1}$ and temperature of 140° C. for 1 hour.

The products were chilled at 0° C. and analyzed by gas chromatograph using flame ionization detector. Results of the reaction are given in Table XIV.

TABLE XIV

Effect of different catalysts on conversion and product selectivity in the isopropylation of m-xylene

| | Catalysts | | | |
|---|---|---|---|---|
| Conversion or selectivity (mole %) | USY | H-Beta | H-Mord | H-ZSM-5 |
| Conversion of m-xylene | 20.7 | 16.5 | 6.0 | 0.1 |
| Selectivity of dimethylcumenes in total products[a] | 90.0 | 97.5 | 91.4 | — |
| Selectivity of 2,4 dimethylcumene among DMC's | 75.8 | 44.1 | 6.5 | — |
| Selectivity of 2,6 dimethylcumene among DMC's | 24.2 | 55.1 | 93.5 | — |
| Selectivity of other products in total products | 10.0 | 2.5 | 8.6 | — |
| 2,4 DMC/2,6 DMC | 3.1 | 0.8 | 0.07 | — |
| % yield of DMC in total products w.r.t. limiting reagent, i.e. isopropylating agent | 74.4 | 64.4 | 54.8 | — |

[a]the remaining products were mainly other isomerised and disproportionated products of xylene along with diisopropyl xylene (DIPX).

EXAMPLE 15

This example illustrates effect of zeolite structure on conversion of o-xylene and the yield of dimethylcumenes. Different catalysts (0.5 g) (Table XV) were loaded into reactor such that the respective catalyst beds were sandwiched between inert porcelain beads. A mixture of o-xylene and isopropyl alcohol with molar ratio 4:1 was introduced into the fixed bed reactors by a syringe pump (Sage Instruments, Model 352, USA) in continuous manner in presence of an inert carrier gas (nitrogen, flow=35 ml/min) at WHSV of 3.24 h$^{-1}$ and temperature of 140° C. for 1 hour.

The products were chilled at 0° C. and analyzed by gas chromatograph using flame ionization detector. Results of the reaction are given in Table XV.

TABLE XV

Effect of different catalysts on conversion and product selectivity in the isopropylation of o-xylene

| | Catalysts | | | |
|---|---|---|---|---|
| Conversion or selectivity (mole %) | USY | H-Beta | H-Mord | H-ZSM-5 |
| Conversion of o-xylene | 24.2 | 15.5 | 7.5 | 0.0 |
| Selectivity of dimethylcumenes in total products[a] | 82.0 | 95.9 | 90.5 | — |
| Selectivity of 3,4 dimethylcumene among DMC's | 94.6 | 88.5 | 97.2 | — |
| Selectivity of 2,3 dimethylcumene among DMC's | 4.2 | 9.7 | 2.8 | — |
| Selectivity of other products in total products | 18.0 | 4.1 | 9.5 | — |
| 3,4 DMC/2,3 DMC | 22.5 | 9.1 | 34.7 | — |
| % yield of DMC in total products w.r.t. limiting reagent, i.e. isopropylating agent | 79.2 | 59.6 | 27.2 | — |

[a]the remaining products were mainly other isomerised and disproportionated products of xylene along with diisopropyl xylene (DIPX).

EXAMPLE 16

This example illustrates use of batch reactor on conversion and product selectivity in isopropylation of p-xylene under autogenous pressure in presence of cyclohexane as solvent using H-Beta catalyst. The reaction was carried out in 100 ml Teflon lined autoclave. A mixture of p-xylene (80 mmol) and isopropyl alcohol (20 mmol) in molar ratio 4:1 was added to 50 g cyclohexane in a beaker. The mixture was then transferred to an autoclave and 0.5 g H-Beta (previously activated at 300° C. in presence of air) was added to the reaction mixture. The autoclave was then sealed and heated for 25 hours at 190° C. oven under self generated pressure. After given reaction time (Table XVI) the autoclave was allowed to cool to room temperature (ca. 2 hours). The solid was extracted with acetone and the mother liquor concentrated in rotavapour.

The concentrated product was analyzed by gas chromatograph (Shimadzu GC-14B) using flame ionization detector and 3 m×⅛" packed column with 5% bentone and 5% DIDP on chromosorb WHP, with mesh size of 801100. Results of reaction are given in Table XVI.

TABLE XVI

Effect of time on stream on conversion and product selectivity in the isopropylation of p-xylene using zeolite H-Beta in batch reactor

| | Reaction time, hours | | | | |
|---|---|---|---|---|---|
| Conversion or selectivity (mole %) | 3 | 7 | 10 | 20 | 25 |
| Conversion of p-xylene | 7.3 | 9.3 | 9.9 | 10.5 | 10.6 |
| Selectivity of dimethylcumenes in total products[a] | 100 | 100 | 100 | 100 | 100 |
| Selectivity of 2,5 dimethylcumene among DMC's | 100 | 100 | 100 | 100 | 100 |
| Selectivity of other products in total products | 0.0 | 0.0 | 0.0 | 0.0 | 0.0 |
| % yield of DMC in total products w.r.t. limiting reagent, i.e. isopropylating agent | 29.2 | 37.2 | 39.6 | 42.0 | 42.4 |

[a]the remaining products were mainly other isomerised and disproportionated products of xylene along with diisopropyl xylene (DIPX).

EXAMPLE 17

This example illustrates effect of time on stream (TOS) on conversion and product selectivity in alkylation of p-xylene using n-propanol as alkylating agent. USY catalyst (0.5 g) was loaded into the reactor such that the catalyst bed was sandwiched between inert porcelain beads. A mixture of p-xylene and n-propanol in a 4:1 molar ratio (Table XVII) was introduced into fixed bed reactor by syringe pump (Sage Instruments, Model 352, USA) in a continuous manner in presence of inert carrier gas (nitrogen, flow=35 ml/min) at a WHSV of 3.24 h$^{-1}$ and a temperature of 140° C. for 1 hour. Product were chilled at 0° C., collected and analyzed by gas chromatograph using flame ionization detector. Results of the reaction are given in Table XVII below.

TABLE XVII

Effect of TOS on conversion and product selectivity in the isopropylation of p-xylene over zeolite USY using n-propanol as alkylating agent

| | Time on stream | | | |
|---|---|---|---|---|
| Conversion or selectivity (mole %) | 1 h | 3 h | 5 h | 8 h |
| Conversion of p-xylene | 6.5 | 5.7 | 4.8 | 3.4 |
| Selectivity of dimethylcumenes in total products[a] | 88.6 | 90.6 | 96.0 | 98.8 |
| Selectivity of 2,5 dimethylcumene among DMC's | 80.5 | 61.0 | 62.0 | 63.0 |
| Selectivity of other products in total products | 11.4 | 9.4 | 4.0 | 1.2 |
| % yield of DMC in total products w.r.t. limiting reagent, i.e. isopropylating agent | 23.0 | 20.7 | 18.4 | 3.4 |

[a] the remaining products were mainly other isomerised and disproportionated products of xylene along with diisopropyl xylene (DIPX).

EXAMPLE 18

This example illustrates effect of time on stream (TOS) on conversion and product selectivity in alkylation of p-xylene using propylene as alkylating agent. USY catalyst (0.5 g) was loaded into the reactor such that the catalyst bed was sandwiched between inert porcelain beads. A mixture of p-xylene and propylene in a 4:1 molar ratio (Table XVIII) was introduced into fixed bed reactor by syringe pump (Sage Instruments, Model 352, USA) in a continuous manner in presence of inert carrier gas (nitrogen, flow=35 ml/min) at a WHSV of 6.48 h$^{-1}$ and a temperature of 140° C. for a period of 8 hours. Product were chilled at 0° C., collected and analyzed by gas chromatograph using flame ionization detector. Results of the reaction are given in Table XVIII.

TABLE XVIII

Effect of TOS on conversion and product selectivity in the isopropylation of p-xylene over zeolite USY using propylene as alkylating agent

| | Time on stream | | | |
|---|---|---|---|---|
| Conversion or selectivity (mole %) | 1 h | 3 h | 5 h | 8 h |
| Conversion of p-xylene | 22.3 | 17.2 | 13.8 | 12.5 |
| Selectivity of dimethylcumenes in total products[a] | 95.4 | 91.8 | 89.6 | 86.4 |
| Selectivity of 2,5 dimethylcumene among DMC's | 98.5 | 98.0 | 99.6 | 100 |
| Selectivity of other products in total products | 4.6 | 8.2 | 10.4 | 13.6 |
| % yield of DMC in total products w.r.t. limiting reagent, i.e. isopropylating agent | 70.0 | 63.2 | 49.6 | 43.2 |

[a] the remaining products were mainly other isomerised and disproportionated products of xylene along with diisopropyl xylene (DIPX).

The salient features of the invention are that the reaction is carried out in a single step by direct contacting a mixture of xylene isomers and alkylating agent in continuous or batch processes with a solid acid zeolite catalyst (preferably USY or Beta). It is observed that the solid acid zeolite catalyst used show high activity and selectivity in the alkylation of all xylene isomers, unlike in the prior art where only o- and not p- or m-xylene could be alkylated.

Advantages of the Invention

1. The catalyst used is eco-friendly, easy to handle, easy to recover and has no or minimal corrosion. As a result disposal of waste is not a problem.
2. The catalysts exhibit high activity and selectivity in alkylation of all xylene isomers and are easily regenerated by thermal treatment in the presence of air.
3. Dimethylcumene isomers are formed with high selectivity.

We claim:

1. A process for the preparation of dimethylcumenes comprising:

alkylating a substrate comprising one or more xylene isomers with an alkylating agent which is selected from the group consisting of propylene, propyl alcohols, and the mixture thereof in the presence of a solid acid zeolite catalyst selected from the group consisting of ultrastable zeolite Y (Si/Al=5 to 50 ratio of Si to Al in zeolite Y) and Beta (Si/Al=10–120 ratio of So Al in zeolite Beta) to produce dimethylcumenes, and separating dimethylcumenes formed in vapour phase.

2. A process as in claim 1 wherein said substrate and alkylating agent are contacted with said solid acid zeolite catalyst at a temperature in the range of 80–250° C. and for a period of at least 1 hour.

3. A process as in claim 1 wherein the product is separated from the vapour phase by condensation at a temperature in the range of 0–3° C.

4. A process as in claim 1 wherein the substrate is selected from the group consisting of o-xylene, m-xylene, p-xylene and any mixture thereof.

5. A process as in claim 1 wherein the Si/Al ratio in said catalyst is between 5 to 20.

6. A process as in claim 2 wherein the temperature of the reaction is in the range of 100–200° C.

7. A process as in claim 2 wherein the temperature of the reaction is in the range of 120–180° C.

8. A process as in claim 1, wherein the molar ratio of xylene substrate to the alkylating agent in the feed is in the range of from 1:2 to 20:1.

9. A process as in claim 8 wherein the molar ratio of xylene substrate to the alkylating agent is in the range of 1:1 to 10:1.

10. A process as in claim 8 wherein the molar ratio of xylene substrate to the alkylating agent is in the range of 1:2 to 5:1.

11. A process as in claim 1 wherein the weight hourly space velocity (WHSV) of the feed is in the range of 0.5 to 30 h$^{-1}$.

12. A process as in claim 11 wherein the weight hourly space velocity (WHSV) of the feed is in the range of 1 to 20 h$^{-1}$.

13. A process as in claim 11 wherein the weight hourly space velocity (WHSV) of the feed is in the range of 2 to 10 h$^{-1}$.

14. A process as in claim 1 wherein the alkylation reaction is carried out in a fixed bed reactor or a batch reactor.

15. A process as in claim 1 wherein p-xylene is alkylated using isopropanol in the presence of zeolite beta catalyst.

16. A process as in claim 1 wherein m-xylene and o-xylene are alkylated using isopropanol as the alkylating agent in the presence of ultrastable zeolite Y (USY) as catalyst.

17. A process as in claim 1 wherein a mixture of p-xylene and isopropyl alcohol in a molar ratio of 4:1 is reacted in a fixed bed reactor in the presence of ultrastable zeolite Y catalyst.

* * * * *